(12) United States Patent
Hascakir et al.

(10) Patent No.: US 10,648,939 B2
(45) Date of Patent: *May 12, 2020

(54) METHOD AND SYSTEM FOR STABILITY DETERMINATION OF ASPHALTENES UTILIZING DIELECTRIC CONSTANT MEASUREMENTS

(71) Applicant: The Texas A&M University System, College Station, TX (US)

(72) Inventors: Berna Hascakir, College Station, TX (US); Abhishek Punase, College Station, TX (US)

(73) Assignee: The Texas A&M University System, College Station, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 16/213,706

(22) Filed: Dec. 7, 2018

(65) Prior Publication Data
US 2019/0113473 A1   Apr. 18, 2019

Related U.S. Application Data

(63) Continuation-in-part of application No. 15/656,757, filed on Jul. 21, 2017.
(Continued)

(51) Int. Cl.
*G01N 27/22* (2006.01)
*G01N 33/28* (2006.01)

(52) U.S. Cl.
CPC .......... *G01N 27/22* (2013.01); *G01N 27/221* (2013.01); *G01N 33/2823* (2013.01)

(58) Field of Classification Search
CPC ... G01N 27/221; G01N 33/2823; G01N 27/22
(Continued)

(56) References Cited

U.S. PATENT DOCUMENTS

| 4,845,976 A | 7/1989 | Johnson et al. |
| 5,420,040 A | 5/1995 | Anfindsen et al. |

(Continued)

FOREIGN PATENT DOCUMENTS

| WO | WO-2015/176007 A1 | 11/2015 |
| WO | WO-2018/017992 A1 | 1/2018 |

OTHER PUBLICATIONS

Hasanvand, Mahdi Zeinali et al; "Developing grey-box model to diagnose asphaltene stability in crude oils: Application of refactive index"; Petroleum; vol. 2; Dec. 30, 2015; pp. 369-380.
(Continued)

*Primary Examiner* — Reena Aurora
(74) *Attorney, Agent, or Firm* — Winstead PC (57) ABSTRACT

A method of determining if unstable asphaltenes are present in a crude oil sample includes obtaining a crude oil sample and performing a fractional analysis of the crude oil sample. In one embodiment, the method further includes measuring, via a cylindrical capacitor, a dielectric constant of the crude oil sample. Responsive to the measured dielectric constant, presence of unstable asphaltenes within the crude oil sample is determined. Responsive to the determined presence of unstable asphaltenes in an amount above a predetermined value, asphaltene precipitation is mitigated by addition of a chemical additive to the well.

20 Claims, 8 Drawing Sheets

Related U.S. Application Data (60) Provisional application No. 62/365,831, filed on Jul. 22, 2016.

(58) Field of Classification Search
USPC .......................................................... 324/686
See application file for complete search history.

(56) References Cited

U.S. PATENT DOCUMENTS

| | | | | |
|---|---|---|---|---|
| 6,642,056 | B1* | 11/2003 | Correra | G01N 33/2805 436/139 |
| 9,347,906 | B2 | 5/2016 | Gruden | |
| 2012/0125087 | A1 | 5/2012 | Sandu et al. | |
| 2013/0341241 | A1 | 12/2013 | Respini et al. | |
| 2017/0020433 | A1 | 1/2017 | Hotaling et al. | |
| 2017/0082594 | A1* | 3/2017 | Blumenshine | G01N 24/08 |
| 2018/0024084 | A1* | 1/2018 | Hascakir | G01N 27/22 324/686 |

OTHER PUBLICATIONS

Wikipedia, LCR meter, Jun. 20, 2016; p. 1-2; retrieved on Sep. 15, 2017, from <https://en.wikipedia.org/w/index.php?title=LCR_meter&oldid=726119545>.

Young, Lee W.; "International Search Report and Written Opinion"; prepared for PCT/US17/43349; dated Sep. 15, 2017; 11 pages.

ASTM, Standard Test Method for Characteristic Groups in Rubber Extender and Processing Oils and Other Petroleum-Derived Oils by the Clay-Gel Absorption Chromatographic Method, Designation D2007-11, May 11, 2015; 8 pages.

Leontaritis, K.J.; Mansoori, G.A.; Jiang, T.S. Asphaltene Deposition in Oil Recovery: A Survey of Field Experiences and Research Approaches. *J. Pet. Sci. Eng.* 1988, 1, 229-239.

Amin, A.; Riding, M.; Sheplar, R.; Smedstad, E.; Ratulowski, J. Subsea Development from Pore to Process. *Oilfield Review* 2005, 17, 4-17.

Akbarzadeh, K.; Hammami, A.; Kharrat, A.; Zhang, D.; Allenson, S.; Creek, J.; Shah, K.; Jamaluddin, A., Marshall, A.G.; Rodgers, R.P.; Mullins, O.C.; Solbakken, T. Asphaltenes Problematic but Rich in Potential. *Oilfield Review* 2007, 19, 22-43.

Sidgwick, N. V. Dipole Moment and Molecular Structure. *Chem. Rev.* 1936, 19, 183-194.

Nelson, R.D. Jr.; Lide, D.R. Jr.; Maryott, A.A. *Selected Values of Electric Dipole Moments for Molecules in the Gas Phase*. National Standard Reference Data System, 1967.

Goual, L.; Firoozabadi, A. Measuring Asphaltenes and Resins, and Dipole Moment in Petroleum Fluids. *AIChE Journal* 2002, 48, 2646-2663.

Wattana, P.; Fogler, H.S.; Yen, A.; Garcia, M.D.C.; Carbognani, L. Characterization of Polarity-Based Asphaltene Subfractions. *Energy and Fuels* 2005, 19, 101-110.

Onsager, L. Electric Moments of Molecules in Liquids. *J. Amer. Chem. Soc.* 1936, 58, 1486-1493.

Clark, F.M. The Properties of Dielectrics. II. The Dielectric Constant. *Journal of the Franklin Institute* 1929, 208, 17-44.

Nalwaya, V.; Tangtayakom, V.; Piumsomboon, P.; Fogler, S. Studies on Asphaltenes through Analysis of Polar Fractions. *Ind. Eng. Chem. Res.* 1999, 38, 964-972.

Prakoso, A.A.; Punase, A.D.; Hascakir, B. A Mechanistic Understanding of Asphaltene Precipitation from Varying Saturate Concentration Perspective. Presented at *SPE Latin American and Carribean Petroleum Engineering Conference*, Nov. 18-20, 2015, Quito, Ecuador. Document ID: SPE-177280-MS.

Mullins, O.C. The Modified Yen Model. *Energy Fuels* 2009, 24, 2179-2207.

Kar, T.; Hascakir, B. The Role of Resins, Asphaltenes, and Water in Water-Oil Emulsion Breaking with Microwave Heating. *Energy and Fuels* 2015, 29, 3684-3690.

Goual, L.; Firoozabadi, A. Effect of Resins and DBSA on Asphaltene Precipitation from Petroleum Fluids. *AIChE Journal* 2004, 50, 470-479.

Swanson, J.M. A Contribution to the Physical Chemistry of the Asphalts. *J. Phys. Chem.* 1942, 46, 141-150.

Maruska, H.P.; Rao, B.M.L. The Role of Polar Species in the Aggregation of Asphaltenes. *Fuel Science and Technology International* 1987, 5, 119-168.

Ese, M.H.; Yang, X.; Sjoblom, J. Film Forming Properties of Asphaltenes and Resins. A Comparative Langmuir-Blodgett Study of Crude Oils from North Sea, European Continent, and Venezuela. *Colloid and Polymer Science* 1998, 276, 800-809.

Evdokimov, I.N.; Losev A.P. Electrical Conductivity and Dielectric Properties of Solid Asphaltenes. *Energy Fuels* 2010, 24, 3959-3969.

Subcommittee D02.04.OC. *Standard Test Method for Characteristic Groups in Rubber Extender and Processing Oils and Other Petroleum-Derived Oils by the Clay-Gel Absorption Chromatographic Method*. ASTM D2007-11 developed for ASTM International: West Conshohocken, PA, 2011.

Jewel, D.M.; Weber, J.H.; Bunger, J.W.; Plancher, H.; Latham, D.R. Ion-Exchange, Coordination, and Adsorption Chromatographic Separation of Heavy-End Petroleum Distillates. *Anal. Chem.* 1972, 44, 1391-1395.

Li, A. Wang, H.; Ouyang, Z.; Cooks, R.G. Paper Spray Ionization using Non-polar Solvents. Supplementary Material for *Chem. Commun.* 2011, 47, 2811-2813.

Prakoso, A.A.; Klock, K.; Punase, A.; Rogel, E.; Ovalles, C.; Hascakir, B. Determination of the Stability of Asphaltenes through Physicochemical Characterization of Asphaltenes. Presented at *SPE Western Regional Meeting*, May 23-26, 2016, Anchorage, Alaska, USA. Document ID: SPE-180422-MS.

Punase, A.; Prakoso, A.A.; Hascakir, B. The Polarity of Crude Oil Fractions Affects the Asphaltenes Stability. Presented at *SPE Western Regional Meeting*, May 23-26, 2016, Anchorage, Alaska, USA. Document ID: SPE-180423-MS.

Barrera, D.M.; Ortiz, D.P.; Yarranton, H.W. Molecular Weight and Density Distributions of Asphaltenes from Crude Oils. *Energy Fuels* 2013, 27, 2474-2487.

Yen, T.F. The Colloidal Aspect of a Macrostructure of Petroleum Asphalt. *Fuel Sci. Technology Int.* 1992, 10, 723-733.

Gawrys, K.L.; Kilpatrick, P.K. Asphaltenic Aggregates are Polydisperse Oblate Cylinders. *Journal of Colloid and Interface Science* 2005, 288, 325-334.

Eyssautier, J.; Levitz, P.; Espinat, D.; Jestin, J.; Gummel, J.; Grillo, I.; Barré, L. Insight into Asphaltene Nanoaggregate Structure Inferred by Small Angle Neutron and X-Ray Scattering. *J. Phys. Chem.* 2011, 115, 6827-6837.

Kumler, W.D. The Dipole Moment of ms-Tetraphenylporphirine. *J. Amer. Chem. Soc.* 1942, 64, 2993-2994.

Sazanovich, I.V.; Galievsky, V.A.; van Hoek, A.; Schaafsma, T.J.; Malinovskii, V.L.; Holten, D.; Chirvony, V.S. Photophysical and Structural Properties of Saddle-shaped Free Base Porphyrins: Evidence for an "Orthogonal" Dipole Moment. *Journal of Physical Chemistry B* 2001, 105, 78187829.

Mullins, O.C.; Seifert, D.J.; Zue, J.Y.; Zeybek, M. Clusters of Asphaltene Nanoaggregates Observed in Oilfield Reservoirs. *Energy Fuels* 2013, 27, 1752-1761.

Cédric Lesaint et al., "Dielectric Properties fo Asphaltene Solutions: Solvency Effect on Conductivity," Energy & Fuels, vol. 27, No. 1 (Nov. 29, 2012).

Siavash Ashoori et al. "The Relationship Between Sara Fractions and Crude Oil Stability," Egyptian Journal of Petroleum, vol. 26, No. 1 (Feb. 3, 2016).

W.M. Haynes et al, "Apparatus for Density and Dielectric Constant Measurements to MPa of Fluids of Cryogenic Interest," Journal of Research of the National Bureau of Standards, vol. 88, No. 4 (Jul. 1, 1983).

* cited by examiner

FIG. 3B
CAPACITANCE - SATURATES

FIG. 3A
CAPACITANCE - AIR

METHOD AND SYSTEM FOR STABILITY DETERMINATION OF ASPHALTENES UTILIZING DIELECTRIC CONSTANT MEASUREMENTS

CROSS REFERENCE TO RELATED APPLICATIONS

The present application is a continuation-in-part of U.S. patent application Ser. No. 15/656,757, filed on Jul. 21, 2017. U.S. patent application Ser. No. 15/656,757 claims priority to U.S. Provisional Patent Application No. 62/365,831, filed on Jul. 22, 2016. U.S. patent application Ser. No. 15/656,757 and U.S. Provisional Patent Application No. 62/365,831 are incorporated herein by reference.

BACKGROUND

Technical Field

The present application relates generally to stability determinations of asphaltenes and more particularly, but not by way of limitation, to methods and systems for making stability determinations of asphaltenes present in crude oil through dielectric constant measurements of polar oil fractions.

History of the Related Art

With continuous rise in energy demand, exploration and production from unconventional reservoirs is gaining high applicability. Heavy oil, extra heavy oil, and bitumen reservoirs contribute to approximately 70% of the world's remaining oil reserves. One challenge associated with crude-oil production from unconventional reservoirs is high asphaltene content in the crude oil. Asphaltenes represent the heaviest and the most polar fraction of crude oil. Interaction of asphaltenes with other fractions of crude oil, such as saturates, aromatics, and resins, can affect the overall polarity and stability of the asphaltenes. Unstable asphaltenes are likely to form solid precipitants in crude oil. Precipitation of unstable asphaltenes can clog reservoir pores and foul downstream production equipment and transportation flow lines causing flow assurance problems and equipment damage.

SUMMARY

The present disclosure relates generally to stability determination of asphaltenes and more particularly, but not by way of limitation, to methods and systems for determining presence of unstable asphaltenes in crude oil through dielectric constant measurements of polar oil fractions. Various aspects of the disclosure relate to a method of determining if unstable asphaltenes are present in a crude oil sample. The method includes obtaining a crude oil sample and performing a fractional analysis of the crude oil sample. In one embodiment, the method further includes measuring, via a cylindrical capacitor, a dielectric constant of the crude oil sample. Responsive to the measured dielectric constant, presence of unstable asphaltenes within the crude oil sample is determined. Responsive to the determined presence of unstable asphaltenes in an amount above a predetermined value, asphaltene precipitation is mitigated by addition of a chemical additive to the well.

Various aspects of the disclosure relate to a method of determining if unstable asphaltenes are present in a crude oil flow. In an embodiment, the method includes placing a crude oil sample obtained from a well in an annulus formed in a cylindrical capacitor. A fractional analysis of the crude oil sample is performed in order to obtain a volume fraction of asphaltenes and deasphalted oil present in the crude oil sample. A colloidal instability index of the crude oil sample is determined. An electrical voltage is applied, via a measuring device, a across the annulus and through the crude oil sample. A dielectric constant of the asphaltenes and the desasphalted oil fractions of the crude oil sample is measured via the measuring device. Responsive to the measured dielectric constant, a presence of unstable asphaltenes within crude oil sample is determined. Responsive to the determined presence of unstable asphaltenes in an amount above a predetermined value, a chemical additive is introduced to the well to mitigate asphaltene instability in the crude oil flow.

Various aspects of the disclosure relate to a method of determining if unstable asphaltenes are present in a crude oil sample. The method includes obtaining a crude oil sample and performing a fractional analysis of the crude oil sample. In one embodiment, the method further includes measuring, via a cylindrical capacitor, a dielectric constant of the crude oil sample. Responsive to the measured dielectric constant, presence of unstable asphaltenes within the crude oil sample is determined. Responsive to the determined presence of unstable asphaltenes in an amount above a predetermined value, asphaltene precipitation is mitigated.

BRIEF DESCRIPTION OF THE DRAWINGS

For a more complete understanding of the present disclosure and for further objects and advantages thereof, reference may now be had to the following description taken in conjunction with the accompanying drawings in which.

DETAILED DESCRIPTION

Various embodiments will now be described more fully with reference to the accompanying drawings. The disclosure may, however, be embodied in many different forms and should not be construed as limited to the embodiments set forth herein.

Asphaltene precipitation represents a significant cost to businesses engaged in crude-oil production and exploration. Due to the complex nature of the molecules constituting asphaltenes, determining asphaltene polarity and thereby predicting asphaltene stability is, however, difficult. A practical way to estimate asphaltene instability would have important implications in predicting reservoir performance. Currently, asphaltene stability is approximated by calculating a "colloidal stability index" which involves calculation of weight percentages of various crude-oil components. This is a very involved analysis that, often times, takes as long as a month to complete.

Figure 1:
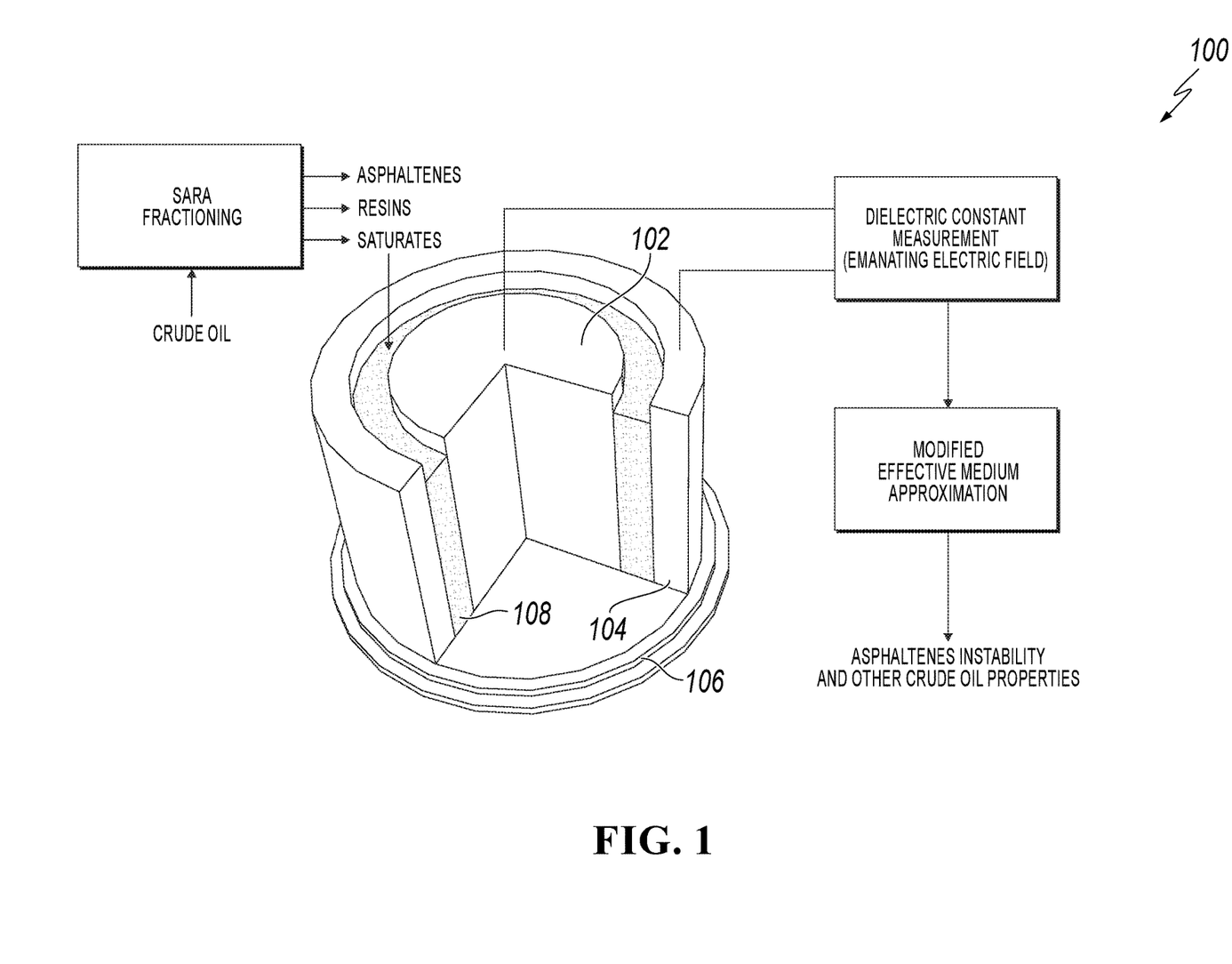
FIG. 1 is a sectional view of a cylindrical capacitor for measuring a dielectric constant of crude oil according to an exemplary embodiment.
Figure 2:
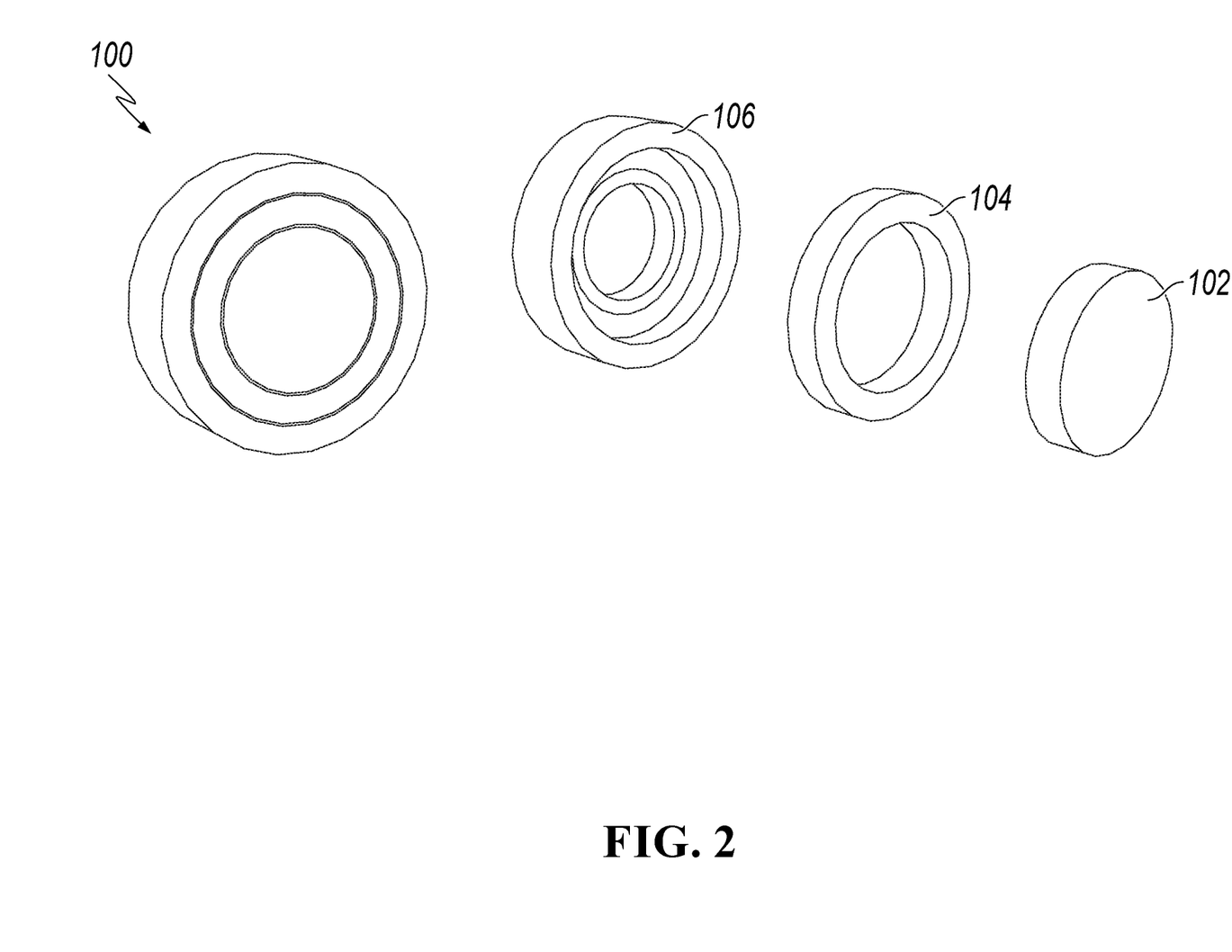
FIG. 2 is an exploded view of the cylindrical capacitor of FIG. 1 according to an exemplary embodiment.

FIG. 1 is a sectional view of a cylindrical capacitor 100 for measuring a dielectric constant of crude oil. FIG. 2 is an exploded view of the cylindrical capacitor 100. Referring to FIGS. 1 and 2 collectively, the cylindrical capacitor 100 includes an inner cylinder 102 and an outer cylinder 104. The inner cylinder 102 and the outer cylinder 104 are arranged generally coaxially thereby defining an annulus 108 there between. In a typical embodiment, the inner cylinder 102 and the outer cylinder 104 are made of a conductive material such as, for example, aluminum; however, in alternative embodiments, the inner cylinder 102 and the outer cylinder 104 may be constructed from any conductive material in accordance with design requirements. The inner cylinder 102 and the outer cylinder 104 are attached to a base 106. In a typical embodiment, the base 106 is constructed from a non-conductive material such as, for example, polytetrafluoroethylene, which is sold, for example, under the name Teflon® by The Chemours Company of Wilmington, Del. In a typical embodiment, the inner cylinder 102 and the outer cylinder 104 are coupled to the base 106 using, for example, RTV-102 white adhesive; however, in alternative embodiments, the inner cylinder 102 and the outer cylinder 104 are coupled to the base 106 using utilizing any non-conductive adhesive or other appropriate bonding agent or process. In certain embodiments, a length of the inner cylinder 102 and the outer cylinder 104 is approximately 0.78 cm whereas a radii of the inner cylinder 102 and outer cylinder 104 are approximately 2 cm and approximately 2.1 cm, respectively. In a typical embodiment, the dimensional correlation between the radii and lengths of the inner cylinder 102 and the outer cylinder 104 is determined by Gauss's flux theorem for a cylindrical charged surface. There is no limitation related to the width of the annulus as long as the dimensions of the capacitor follow Equation 1, the annulus width may be modified as per the requirement. The overall capacitance for this specific geometry is given by Equation 1.

$$C = \frac{2\pi\epsilon_0 \epsilon L}{\ln\left(\frac{b}{a}\right)} \qquad \text{Equation 1}$$

Where C is the capacitance (F), $\epsilon_0$ is the permittivity of a vacuum ($8.85 \times 10^{-12}$ F/m), $\epsilon$ is the dielectric constant of a sample present in the annulus 108, L is the length of the cylinders (in meters), a is the radius of the inner cylinder 102 (in meters), and b is inner the radius of the outer cylinder 104 (in meters). A cylindrical capacitor presents the advantage of easily containing and measuring the dielectric constant of both liquid as well as solid test samples within the annulus (108) created by the inner cylinder 102 and the outer cylinder 104.

Figure 3A:
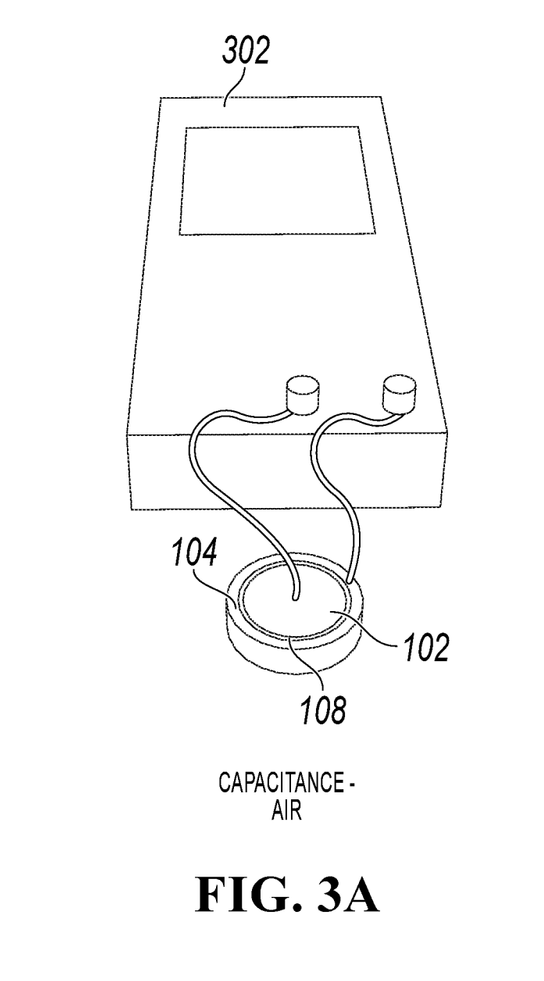
FIGS. 3A and 3B are illustrations of the steps involved in calculating a dielectric constant of a crude oil sample according to an exemplary embodiment.
Figure 3B:
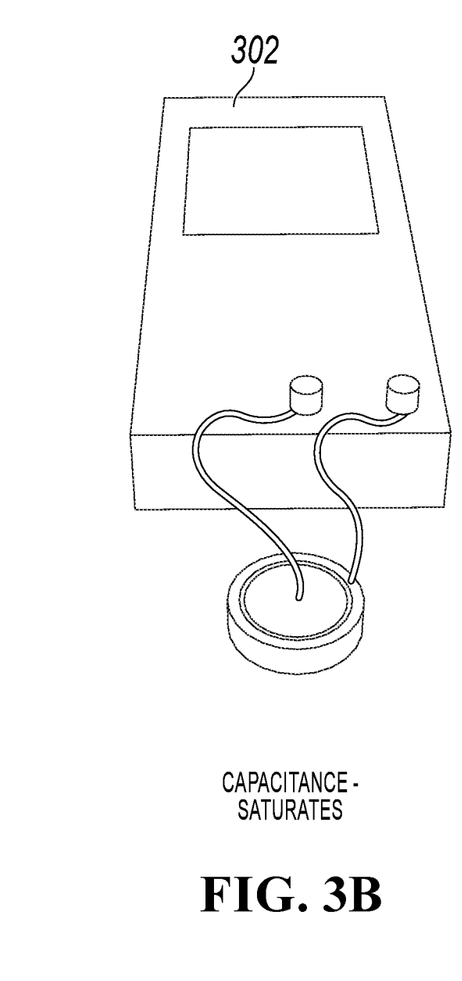

FIGS. 3A and 3B illustrate steps of determining the dielectric constant of a test sample. During operation, the inner cylinder 102 and the outer cylinder 104 are connected to respective leads of a measuring device 302. In a typical embodiment, the measuring device 302 is, for example, a multimeter; however, in alternative embodiments, any capacitance meter can be used to measure the overall capacitance of the test sample. In a first step, the annulus 108 of the cylindrical capacitor 100 is empty and the measuring device applies an electrical voltage across the annulus 108 to measure a capacitance of air ($C_{Air}$). In a second step, the annulus 108 is completely filled with a test sample such as, for example, crude oil sampled from a production well head or a production flow line. The measuring device 302 is applies an electrical voltage across the annulus and measures the capacitance of the sample ($C_{sample}$). During operation, all the dimensional parameters of the cylindrical capacitor 100 and the permittivity of vacuum remain unchanged, thus the ratio of the measured capacitances ($C_{sample}/C_{Air}$) calculates a dielectric constant of the test sample. In various embodiments, the measuring device 302 provides a measurement of a dielectric constant of the crude oil sample, provide a measurement of asphaltene stability, or provide an alert to an operator of a high probability of asphaltene instability. In other embodiments, the measuring device 202 and/or the cylindrical capacitor 100 may be embodied within a crude-oil pipeline or other equipment coupled to a crude-oil pipeline.

Still referring to FIGS. 3A-3B, in certain embodiments, the dielectric constant of solid materials may include errors generated by air that is present in the pore space of the solid materials. In various embodiments, the measuring device 302 corrects the dielectric constant for this type of error by using a density correlation. The density value is used in conjunction with the measured density value as in Equation 2 (Table 1 provides a comparison of measured dielectric constants with literature values).

TABLE 1

Comparison of the Measured Dielectric Constants with Data Compiled from Literature

| | Dielectric Constants | |
|---|---|---|
| Material | Measured Value | Value from literature |
| n-pentane | 1.76 | 1.84 |
| n-hexane | 1.80 | 1.88 |
| n-heptane | 1.82 | 1.90 |
| n-decane | 1.86 | 2.00 |
| toluene | 1.93 | 2.40 |
| Sodium Chloride* | 5.20 | 5.50 |
| Potassium Chloride* | 4.65 | 4.50 |

*The dielectric constants of solid samples were corrected by excluding the contribution of air in the pores of the solid materials $$\epsilon_{corrected} = (\epsilon_{measured} - 1)\left(\frac{\rho_{solid}}{\rho_{measured}}\right) + 1 \qquad \text{Equation 2}$$

Where $\epsilon$ and $\rho$ denotes the dielectric constant and density, respectively. The subscript "measured" signifies the measured parameter value in the laboratory which includes the contribution of air in the pore space of the samples, and the subscript "solid" represents the compiled parameter value of the solid material from literature. The measured and literature-provided values of the chemicals listed in Table 1 show good matches which highlight the accuracy of the cylindrical capacitor 100 in measuring dielectric constants for both solid and liquid samples. In a typical embodiment, the cylindrical capacitor 100 and the measuring device 302 can be utilized to estimate the dielectric constant of a bulk crude oil samples as well as individual fractions of the bulk crude oil sample including, for example, saturates, aromatics, resins, and asphaltenes. The dielectric constant of bulk crude oil can also be measured by introducing it directly in the capacitor annulus.

Figure 4A:
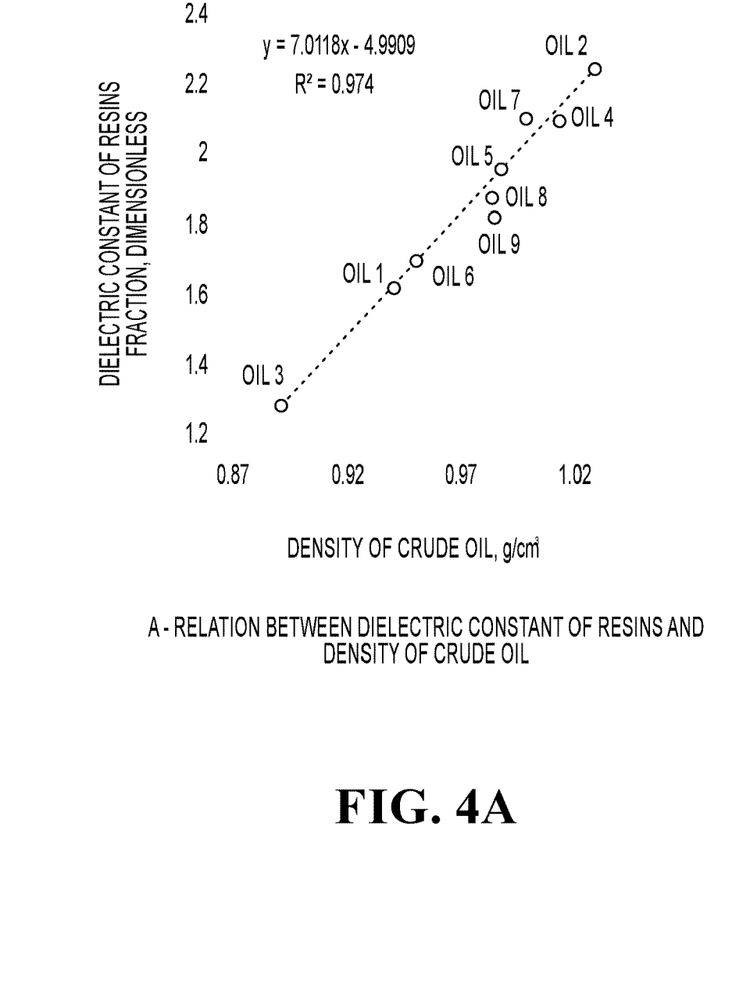
FIG. 4A is a plot of dielectric constant versus crude-oil density.
Figure 4B:
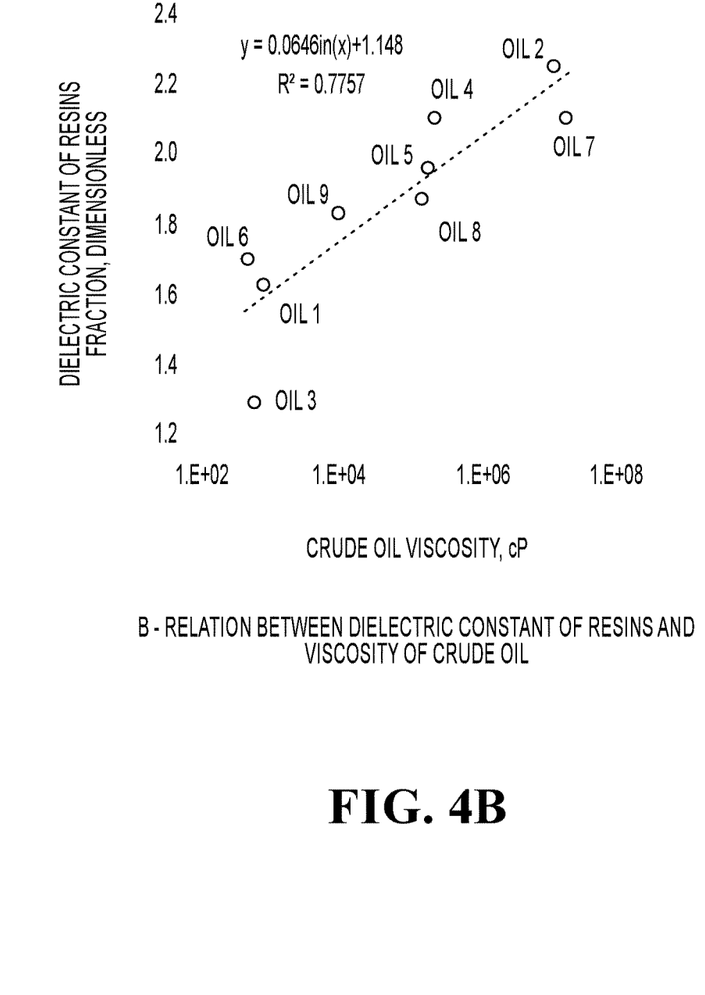
FIG. 4B is a plot of dielectric constant versus crude-oil viscosity.

FIG. 4A is a plot of dielectric constant versus crude-oil density. FIG. 4B is a plot of dielectric constant versus crude-oil viscosity. In various embodiments, a higher degree of coherence between physical properties of the crude oil and the dielectric constant of the resins fraction as compared to an asphaltene fraction may arise due to impurities present within or along-with the asphaltene molecules. In certain embodiments, the density of asphaltenes is measured by calculating the density of asphaltene-toluene mixtures for known volume and mass fraction of toluene. Table 2 provides sample density data that is used by FIGS. 4A and 4B.

the fact that polarity is indicative of intermolecular forces of attraction. A comparative analysis of the dielectric constants of saturates, resins, and asphaltenes fractions (Table 3) with density and viscosity of crude oil (Table 2) to evaluate the effect of crude oil physical characteristic on the dielectric constant of individual fractions is depicted in FIGS. 4A and 4B. As illustrated in FIGS. 4A and 4B, the dielectric constant of resins exhibits strong correlation with the density as well as the viscosity of the crude oil sample.

In certain embodiments, a higher degree of coherence between the physical properties of the crude oil sample and the dielectric constant of resins fraction as compared to asphaltenes fraction may arise due to impurities present within or along with the asphaltene molecules. Within the reservoir environment, the most polar asphaltene fraction of the crude oil can physically and chemically interact with different minerals present in, for example, reservoir rocks, clays, and brines. Interactions of asphaltene fractions can increase the presence of polar molecules and ultimately increase the dielectric constant value for asphaltenes fractions. In certain embodiments, resins fractions including

TABLE 2

Characterization of Crude Oil Samples and Asphaltenes Density

| Sample # | Gravity, *API | Viscosity, cP* | Crude Oil Components based on ASTM D2007-11, wt. % | | | | Asphaltenes Density, gm/cm³ |
|---|---|---|---|---|---|---|---|
| | | | Saturates | Aromatics | Resins | Asphaltenes | |
| OIL 1 | 18.84 | 884 | 22.63 | 37.57 | 16.03 | 23.76 | 1.16 |
| OIL 2 | 6.11 | 12,100,000 | 10.68 | 29.10 | 20.14 | 40.08 | 1.12 |
| OIL 3 | 27.05 | 676 | 24.28 | 25.00 | 5.430 | 45.30 | 0.95 |
| OIL 4 | 7.97 | 251,000 | 12.70 | 42.11 | 22.93 | 22.26 | 1.18 |
| OIL 5 | 11.56 | 209,000 | 10.14 | 38.01 | 13.09 | 38.76 | 1.16 |
| OIL 6 | 17.12 | 496 | 30.03 | 41.84 | 15.56 | 12.57 | 1.21 |
| OIL 7 | 10.01 | 19,200,000 | 11.05 | 30.47 | 16.06 | 42.41 | 1.15 |
| OIL 8 | 12.19 | 168,000 | 11.01 | 44.89 | 20.75 | 23.35 | 1.16 |
| OIL 9 | 12.09 | 10,100 | 16.51 | 37.81 | 17.10 | 28.58 | 1.28 |

*Viscosity values are given at ambient conditions and were obtained through viscosity-temperature correlations due to limitations of the equipment. Similarly all API gravity values were also estimated using density-temperature correlations to obtain value at standard conditions. Relative error range for the measurements are ±0.15%, ±1%, ±15% for API gravity, viscosity, and SARA fractionation, respectively.

TABLE 3

Measured Dielectric Constants of Bulk Crude Oil Samples and Deasphalted Oil, Saturates, Resins, and Asphaltenes Fractions of Crude Oils

| Sample Name | Dielectric Constants* | | | | |
|---|---|---|---|---|---|
| | Crude Oil | Deasphalted Oil (DAO) | Saturates | Resins | Asphaltenes |
| OIL 1 | 2.31 | 2.52 | 1.84 | 1.62 | 4.22 |
| OIL 2 | 2.12 | 2.28 | 1.84 | 2.25 | 3.23 |
| OIL 3 | 1.72 | 1.88 | 1.55 | 1.28 | 4.57 |
| OIL 4 | 2.09 | 2.34 | 1.73 | 2.10 | 3.77 |
| OIL 5 | 2.07 | 2.49 | 1.78 | 1.96 | 3.56 |
| OIL 6 | 2.34 | 2.44 | 1.85 | 1.69 | 5.01 |
| OIL 7 | 1.81 | 3.45 | 1.53 | 2.10 | 3.94 |
| OIL 8 | 1.93 | 2.31 | 1.82 | 1.87 | 3.75 |
| OIL 9 | 2.00 | 2.45 | 1.78 | 1.83 | 4.90 |

*The dielectric constants of the aromatics fraction could not be obtained due to low amount of aromatics collection at the end of each fractionation method.

Still referring to FIGS. 4A and 4B, in certain embodiments, the dielectric constant may be used as an indirect measure of the polarity of each component in the crude oil. Table 3 contains sample data used to plot FIGS. 4A and 4B. In a typical embodiment, the physical properties of the crude oil sample reflect how polar the crude oil sample is due to mainly organic constituents provide a better representation of the organic origin of the crude oil due to physical properties of crude oils being dominated by the organic constituents. Thus, in a typical embodiment, crude oil samples having an asphaltenes fraction with a higher dielectric constant are generally less stable than crude oil samples having an asphaltenes fraction having a lower dielectric constant. Higher dielectric constants indicate higher polarity which indicates a higher possibility of asphaltenes to come together and precipitate.

In a typical embodiment, two alternative parameters are utilized to gain a relative measurement of the dielectric constant of an asphaltene fraction of a crude oil sample. These parameters are the Lowry Parameter and the Wu Parameter. Traditionally, the Lowry parameter has been determined according to Equations 3. Similarly, the Wu Parameter has been determined according to Equation 4.

$$\text{LowryParameter} = v_{asphaltene} \varepsilon_{asphaltene} + v_{DAO} \varepsilon_{DAO} \quad \text{Equation 3}$$

$$\text{WuParameter} = 10^{log(v_{asphaltene} \varepsilon_{asphaltene}) + log(v_{DAO} \varepsilon_{DAO})} \quad \text{Equation 4}$$

Where $v$ and $\varepsilon$ denote the volume fraction and dielectric constant, respectively, of asphaltenes and deasphalted oil (DAO) in the crude oil mixture. It has been found, however, that calculating the Lowry Parameter and the Wu Parameter utilizing Equations 3 and 4 is insufficient as Equations 3 and 4 overestimate the overall dielectric constant values of a bulk oil mixture. Thus, in the exemplary method, a modified Lowry Parameter or a modified Wu Parameter are calculated by the measuring device 302 according to equations 5 and 6.

$$\text{Modified Lowry Parameter} = v_{Asphaltenes}\varepsilon_{Asphaltenes} - v_{DAO}\varepsilon_{DAO} \quad \text{Equation 5}$$

$$\text{Modified Wu Parameter} = 10^{(\log 10(v_{Asphaltenes}\varepsilon_{asphaltene}) - \log 10(v_{DAO}\varepsilon_{DAO})} \quad \text{Equation 6}$$

In a typical embodiment, a crude oil sample having a modified Lowry Parameter greater than 0 has a high probability of containing unstable asphaltenes. Likewise, a crude oil sample having a modified Wu parameter greater than 1 has a high probability of containing unstable asphaltenes. In various embodiments, the measuring device 302 calculates the modified Lowry parameter and the modified Wu parameter and returns a measurement to an operator.

Figure 5A:
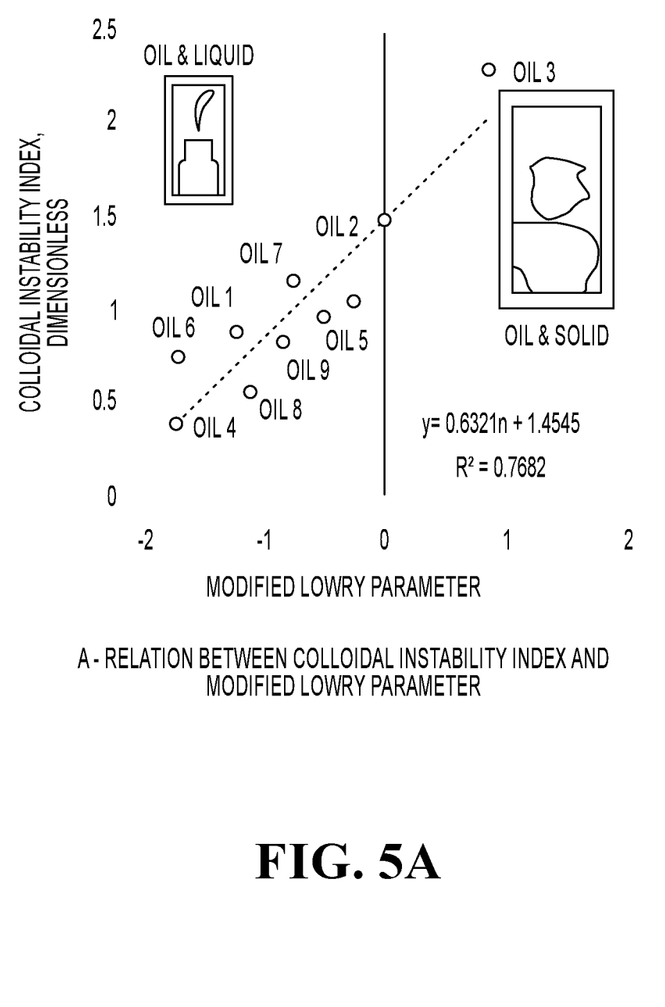
FIG. 5A is a plot of colloidal instability index (CII) versus modified Lowry Parameter.
Figure 5B:
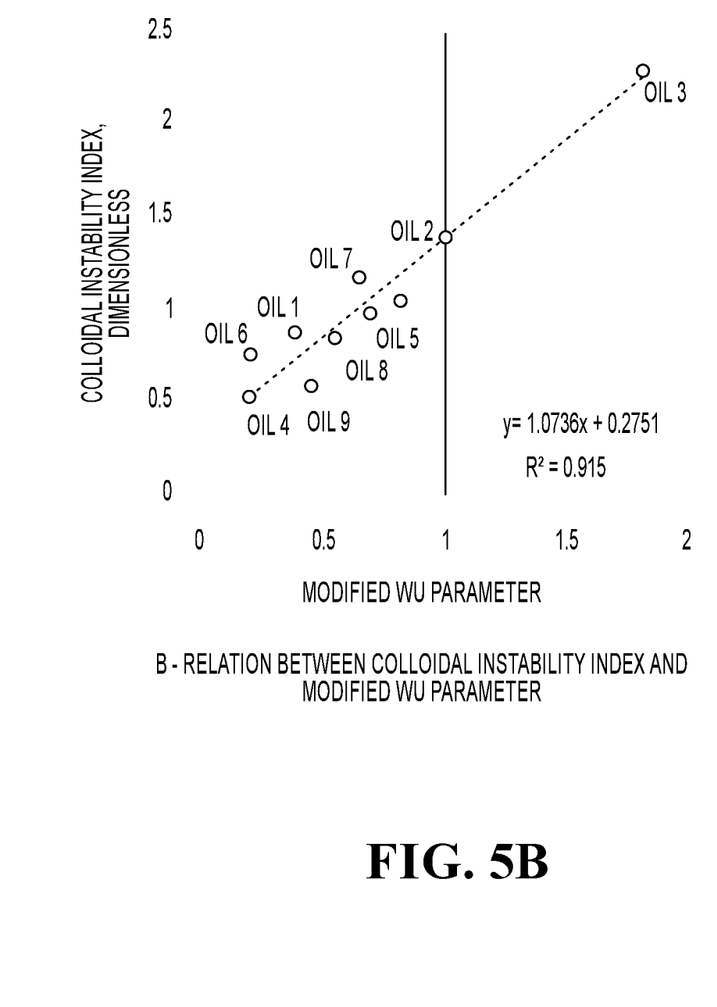
FIG. 5B is a plot of CII versus modified Wu Parameter.

It has been found that asphaltenes and saturates contribute to asphaltene instability while aromatics and resins contribute to asphaltene stability. To that end, an embodiment utilizes a measurement of Colloidal Instability Index (CII). FIG. 5A is a plot of CII versus modified Lowry Parameter. FIG. 5B is a plot of CII versus modified Wu Parameter. The calculated amounts are derived from modified Lowry or Wu Parameters (Equations 5 and 6). As previously noted, this distinction is made because each of the respective original parameter overestimates the overall dielectric constant values of a bulk oil mixture. The modified Lowry or Wu parameter is used to directly describe the overall stability of asphaltenes within the bulk crude oil. Quantitative assessment of the overall asphaltenes stability is carried out based on the dielectric constant values of the asphaltenes and deasphalted oil fractions. Thus the dielectric constant of pure state asphaltenes and DAO fractions is utilized to assess stability.

The Colloidal Instability Index is calculated based on data given in Table 2 to yield FIGS. 5A and 5B. CII considers the crude oil mixture as a colloidal solution made of asphaltenes, asphaltene flocculants (saturates), and asphaltenes peptizers (aromatics and resins). Equation 7 provides the mathematical definition of CII, where the terms represent weight percentages of each fraction within the crude oil. In a typical embodiment, the weight percentages of each fraction within the crude oil sample is determined via a SARA analysis according to, for example, ASTM D-2007-11.

$$CII = \frac{(\text{Asphaltenes} + \text{Saturates})}{(\text{Aromatic} + \text{Resins})} \quad \text{Equation 7}$$

Still referring to FIGS. 5A and 5B, an increase in CII indicates lower stability and higher propensity of asphaltenes to precipitate within the crude oil mixture. The data used to calculate FIGS. 5A and 5B was all taken from the data presented in Tables 2 and 3. Direct linear correlation can be observed between the CII and the modified Lowry and Wu parameters, highlighting that the asphaltenes become more unstable at higher modified parameter values. In certain embodiments, the modified Wu parameter, shown in FIG. 5B, exhibits a higher degree of coherence with CII as compared to the modified Lowry parameter, shown in FIG. 5A. It has been found that a colloidal instability index higher than approximately 1.5 is a threshold for asphaltene stability. Thus, a modified Lowry parameter greater than zero and the colloidal instability index greater than 1.5 determines instable asphaltenes that are likely to precipitate. Similarly, a modified Wu parameter greater than 1 and having a CII higher than 1.5 determines the unstable asphaltenes that are likely to precipitate.

Figure 6A:
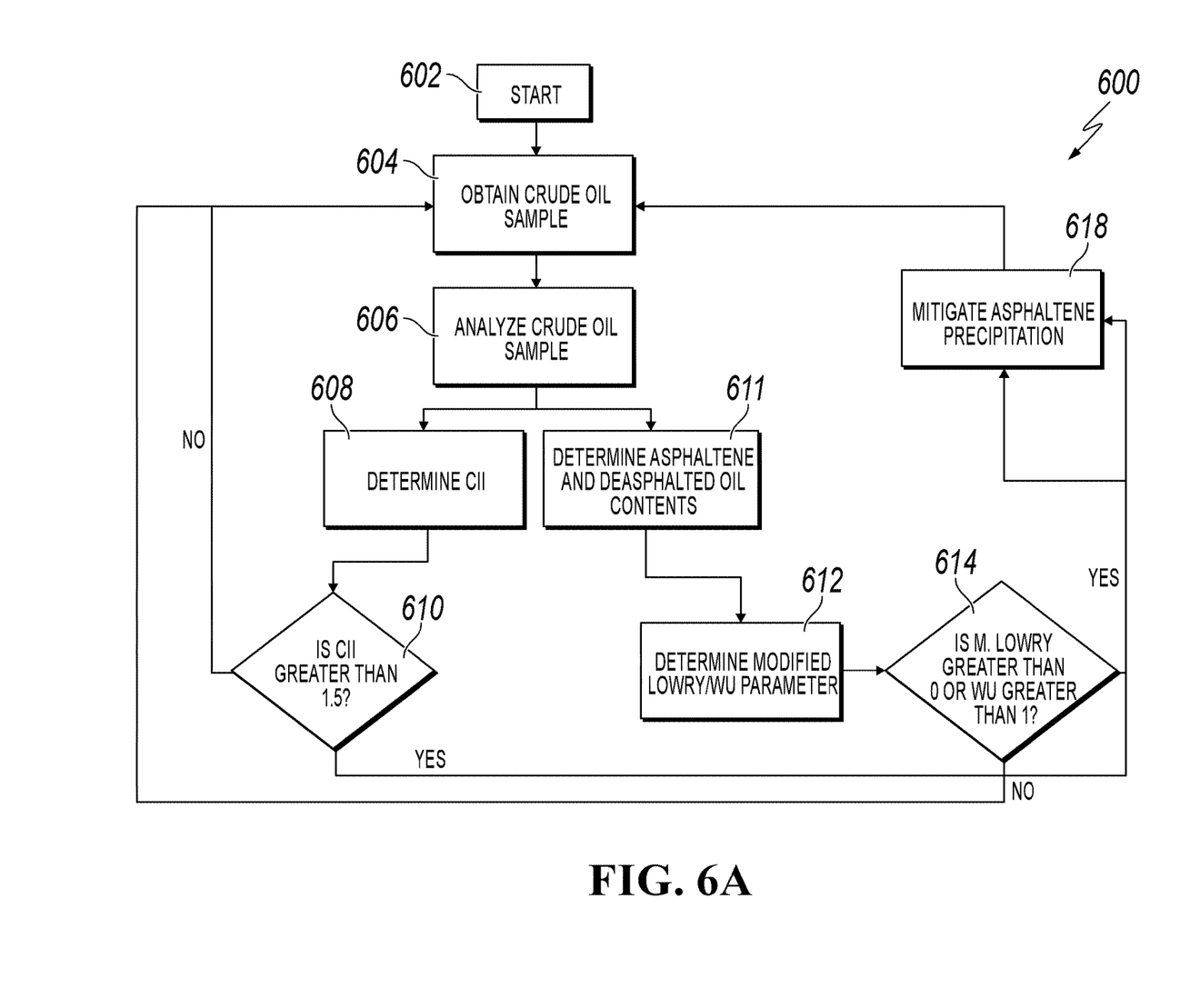
FIG. 6A is a flow diagram of a process for determining asphaltene stability of a crude oil sample according to an exemplary embodiment.

FIG. 6A is a flow diagram illustrating one embodiment of a process 600 for determining presence of unstable asphaltenes in a crude oil sample. The process 600 begins at step 602. At step 604, a crude oil sample is obtained from, for example, a production well. At step 606, a SARA analysis is performed on the crude oil sample to determine a fractional composition of the crude oil sample. In a typical embodiment, the SARA analysis of step 606 is performed according to, for example, ASTM D-2007-11 discussed above. At step 608, a CII is determined by the measuring device 302 according to Equation 7. At step 610, it is determined by the measuring device 302 if the CII is greater than 1.5. If, in step 610, the CII is determined by the measuring device 302 to be less than 1.5, the process returns to step 604. If, in step 610, the CII is determined by the measuring device 302 to be greater than 1.5, then the process 600 proceeds to step 618. At step 618, responsive to an indication of unstable asphaltenes being present in the crude oil sample, actions are taken to mitigate asphaltene precipitation such as, for example, modulation of temperature, pressure, chemical content, or any combination thereof.

Alternatively, from step 606, the process 600 proceeds to step 611. At step 611, a content of asphaltenes and deasphalted oil present in the crude oil sample is determined by the measuring device 302. At step 612, the modified Lowry or modified Wu parameter is determined using the cylindrical capacitor 100 and the measuring device 302 described above with respect to FIGS. 1 and 2. At step 614, the measuring device 302 determines if the modified Lowry Parameter is greater than 0 or, alternatively, if the modified Wu Parameter is greater than 1. At step 614, if the measuring device 302 determines that the modified Lowry Parameter is greater than 0, or the modified Wu Parameter is greater than 1, the process 600 proceeds to step 618. Responsive to an indication of unstable asphaltenes being present in the crude oil sample, the measuring device 302 may, in various embodiments, alert an operator to a high probability of asphaltene instability. A modified Lowry Parameter greater than 0 or a modified Wu Parameter greater than 1 is indicative of unstable asphaltenes that are likely to precipitate. At step 618, responsive to an indication of asphaltene instability, actions are taken to mitigate asphaltene precipitation such as, for example, modulation of temperature, pressure, chemical content, or any combination thereof. If, at step 614, the measuring device 302 determines that the modified Lowry Parameter is less than 0 or the modified Wu Parameter is less than 1, the process 600 returns to step 604. A modified Lowry Parameter less than 0 or a modified Wu Parameter less than 1 is indicative of stable asphaltenes that are unlikely to precipitate.

Figure 6B:
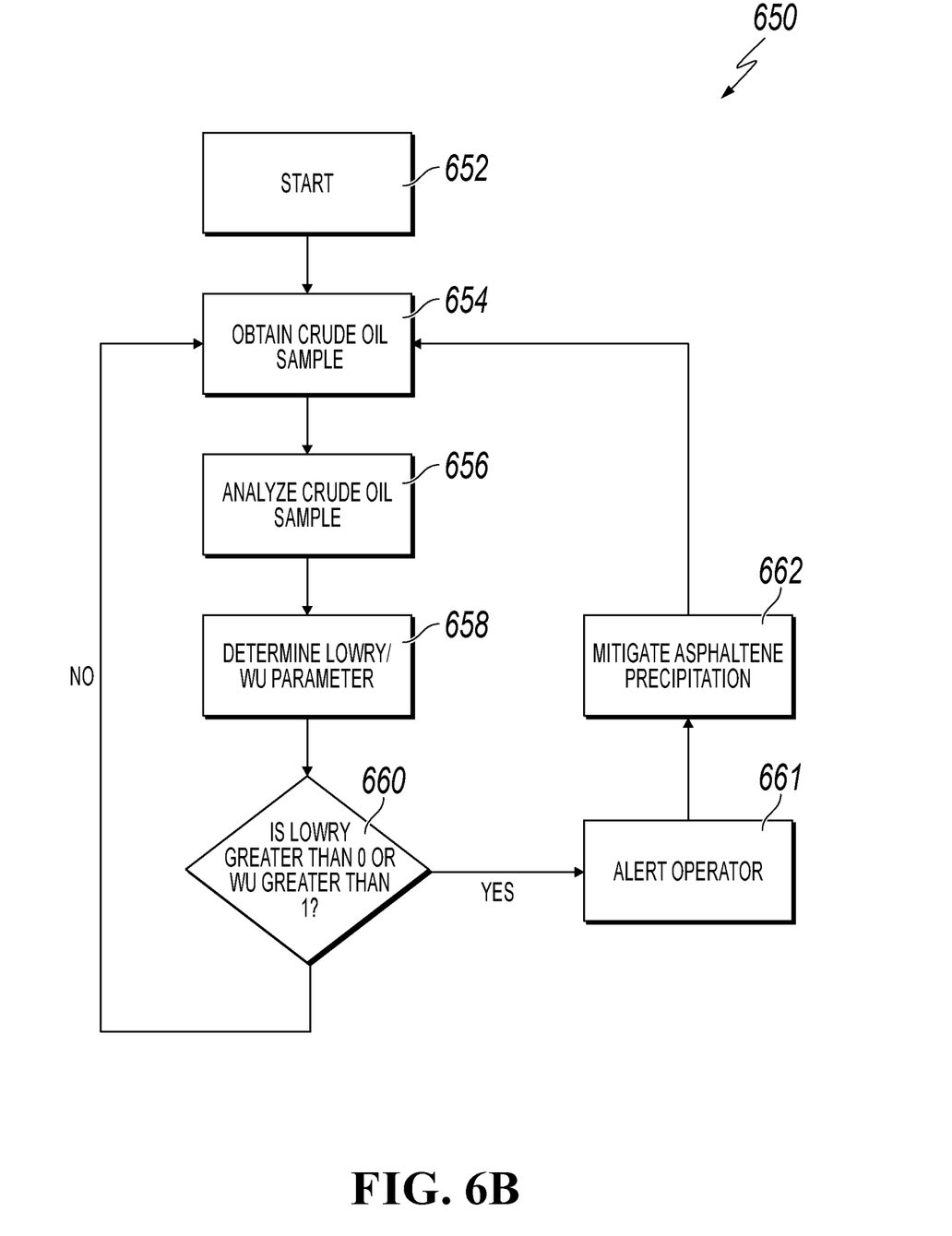
FIG. 6B is a flow diagram of a process for determining asphaltene stability of a crude oil sample according to an exemplary embodiment.

FIG. 6B is a flow diagram illustrating another embodiment of a process 650 for determining presence of unstable asphaltenes in a crude oil sample. The process 650 begins a step 652. At step 654, a crude oil sample is obtained from, for example, a production well. At step 656, the crude oil is analyzed to determine a weight percent asphaltenes content of the crude oil sample. In a typical embodiment, procedure described in ASTM D2007-11 is followed to determine the asphaltene content by weight percent of crude oil. In a typical embodiment, the dielectric constant is determined using the cylindrical capacitor 100 described above with respect to FIGS. 1 and 2. At step 658, the measuring device 302 determines at least one of a modified Lowry Parameter and a modified Wu Parameter. In a typical embodiment, determination of at least one of the modified Lowry Parameter and the modified Wu Parameter facilitates approximation of the dielectric constant of the crude-oil sample. At step 660, the measuring device 302 determines if the modified Lowry Parameter is greater than 0 or, alternatively, if the modified Wu Parameter is greater than 1. At step 660, if the modified Lowry Parameter is greater than 0, or the modified Wu Parameter is greater than 1, the process 650 proceeds to step 661. At step 661, responsive to a determination by the measuring device 302 that a modified Lowry Parameter is greater than 0 or a modified Wu Parameter is greater than 1, the measuring device 302 alerts an operator to a high probability of asphaltene instability. A modified Lowry Parameter greater than 0 or a modified Wu Parameter greater than 1 is indicative of unstable asphaltenes that are likely to precipitate. At step 662, actions are taken to mitigate asphaltene precipitation such as, for example, modulation of temperature, pressure, chemical content, or any combination thereof. After actions are taken to mitigate asphaltene precipitation in step 662, the process 650 returns to step 654.

If, at step 660, the measuring device 302 determines that the modified Lowry Parameter is less than 0 or the modified Wu Parameter is less than 1, the process 650 returns to step 654. A modified Lowry Parameter less than 0 or a modified Wu Parameter less than 1 is indicative of stable asphaltenes that are unlikely to precipitate. In one embodiment, the modified Lowry Parameter or the modified Wu parameter is used as a proxy for the dielectric constant of the crude-oil sample, which allows determination of asphaltene stability in approximately 1 minute or less.

Referring to FIGS. 6A and 6B collectively, it is contemplated that at least one of the modified Lowry Parameter, the modified Wu Parameter, or the CII will be measured periodically during, for example, production of an active well, delivery of crude oil to a refinery, or operation of a refinery. By observing trends over time of the modified Lowry Parameter, the modified Wu Parameter, or the CII, changes in the composition of the crude oil and, particularly, changes in asphaltene stability over time can be observed. For example, if the modified Lowry Parameter or the modified Wu Parameter begins to rise, well or refinery operators will be signaled by, for example, the measuring device 302, to take action to mitigate the possibility of asphaltene precipitation such as, for example, modulating a temperature or pressure of the crude oil reservoir, adjusting the chemical composition of the crude oil flow, or any combination thereof.

Figure 7:
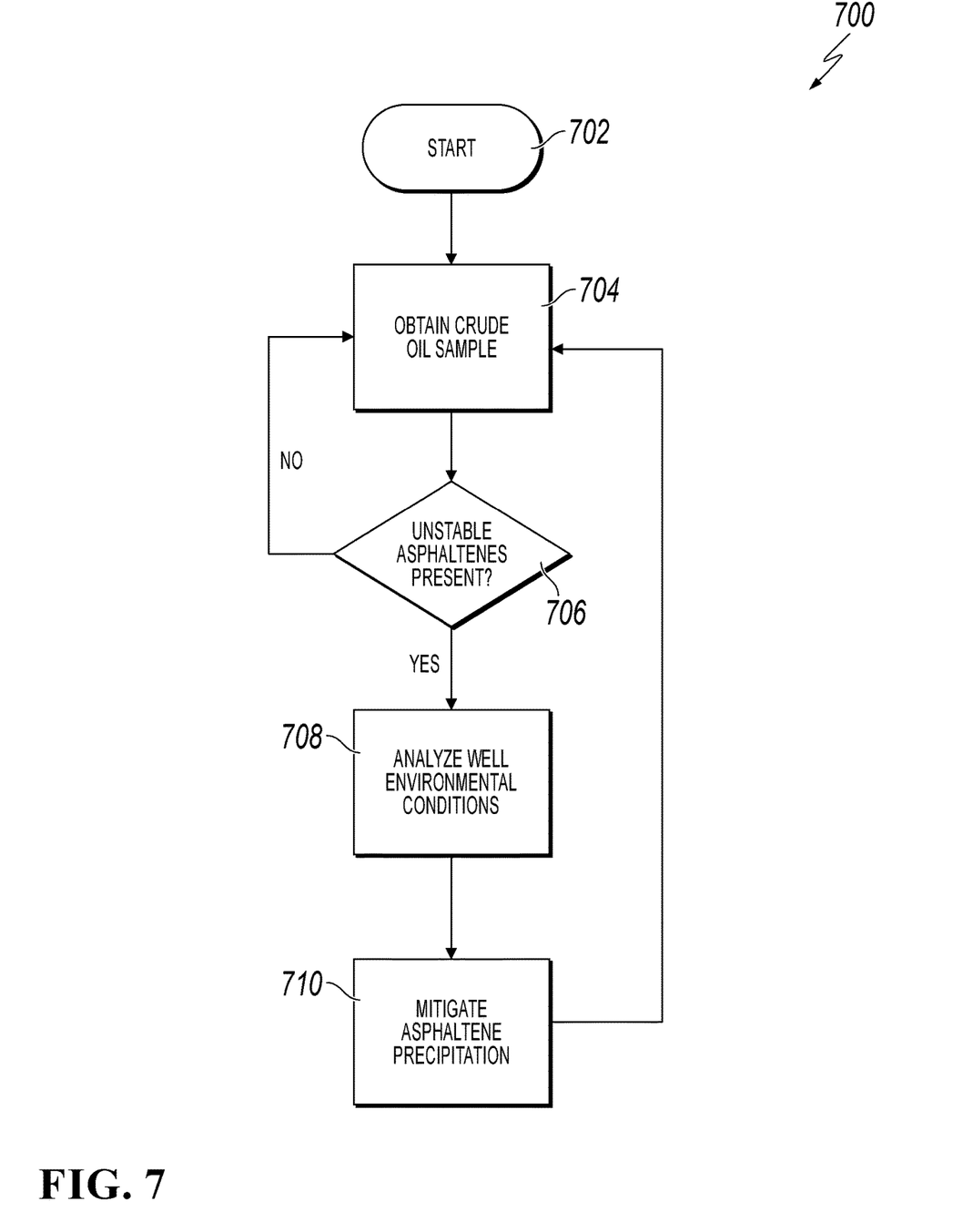
FIG. 7 is a flow diagram illustrating a testing a mitigation cycle according to an exemplary embodiment.

FIG. 7 is a flow diagram illustrating an embodiment of a testing a mitigation cycle 700. The cycle 700 begins at step 702. At step 704, a crude oil sample is obtained. At step 706, an analysis is performed in an effort to detect the presence of unstable asphaltenes in the crude oil sample. In various embodiments, the analysis could be performed according to the process 600 described above in FIG. 6A or the process 650 described above in FIG. 6B. If at step 706, it is determined that unstable asphaltenes are not present in the crude oil sample, the cycle 700 returns to step 704 where the cycle is repeated at a periodic interval. In various embodiments, the periodic interval could be, for example, daily, twice daily, or any other time period as dictated by a particular well or refinery environment. In other embodiments, step 704 could be triggered by various production conditions such as, for example, a detected change in reservoir rock, a detected change in well temperature, a detected change in well pressure, or a detected amount of unstable asphaltenes. In a related embodiment, step 706 determines an amount of unstable asphaltenes in the crude oil sample and, if the amount of unstable asphaltenes is at or below a predetermined value, the cycle 700 returns to step 704. If, at step 706, it is determined that unstable asphaltenes are present in the crude oil sample, the cycle 700 proceeds to step 708. In yet another embodiment, the step 706 determines an amount of unstable asphaltenes present in the crude oil sample. If the amount of unstable asphaltenes is above a predetermined value, the cycle 700 proceeds to step 708. The predetermined value may be adjusted to account for environmental values of the surrounding structure of the well and/or reservoir, or may be based on economic value/impact of using certain chemical additives in the mitigation of asphaltene precipitation.

Still referring to FIG. 7, at step 708, well environmental conditions are analyzed. Often, a specific chemical additive necessary to mitigate asphaltene precipitation is dependent, at least in part, on well environmental factors including, for example, chemistry of the surrounding reservoir rock and/or an ambient temperature of a transmission pipeline. Thus, in various embodiments, a reservoir accessed through a land-based wellhead may require a different chemical additive than a reservoir accessed through a sub-sea wellhead due in part to differences in the surrounding ambient temperature. Furthermore, in some situations utilization of chemical additives having, for example, straight-chain hydrocarbons can aggravate asphaltene precipitation and increase the risk of equipment damage. In various embodiments, step 708 may include analysis of drilling mud and well cuttings in an effort to determine well environmental conditions. From step 708, the cycle 700 proceed to step 710.

At step 710, mitigation is undertaken to reduce the likelihood of asphaltene precipitation. In one embodiment, a chemical additive such as, for example, aromatic hydrocarbons, may be injected into the well from which the crude oil sample was obtained in an effort to mitigate asphaltene precipitation. In a related embodiment, the chemical additive is injected into a region of the well that is in close proximity to a wellhead at an oil reservoir. In another embodiment, a chemical additive used to mitigate asphaltene precipitation is injected into a region of the well that is in close proximity to an area where temperature changes may affect asphaltene precipitation. For example, the chemical additive may be injected into a region of the well that is in close proximity to where a sub-sea well exits the sea floor to the sea. The chemical additive utilized and/or an amount of the chemical additive may, in various embodiments, be determined in part from the well environmental conditions analysis described in step 708 in addition to the process 600 described above in FIG. 6A and the process 650 described above in FIG. 6B. Thus, the process 600 described above in FIG. 6A and the process 650 described above in FIG. 6B are beneficial in aiding the determination of a specific chemical additive that is effective for mitigating asphaltene precipitation under a particular set of well conditions.

In an alternative embodiment, step 710 mitigates asphaltene precipitation by modifying pressure at a region of the well that is in close proximity to the wellhead at the reservoir. In a related embodiment, step 710 mitigates asphaltene precipitation by modifying pressure and injecting a chemical additive into the well. In another embodiment, step 710 mitigates asphaltene precipitation by modifying the pressure and injecting a chemical additive into the well at a region of the well that is in close proximity to the wellhead at the reservoir.

From step 710, the cycle returns to step 704 where another crude oil sample is obtained. Repetition of the cycle 700 allows feedback to evaluate the efficacy of the chemical additive at mitigating asphaltene precipitation. Such feedback facilitates, if necessary further adjustment of steps taken to mitigate asphaltene precipitation.

Although various embodiments of the method and system of the present disclosure have been illustrated in the accompanying Drawings and described in the foregoing Specification, it will be understood that the disclosure is not limited to the embodiments disclosed, but is capable of numerous rearrangements, modifications, and substitutions without departing from the spirit and scope of the disclosure as set forth herein. It is intended that the Specification and examples be considered as illustrative only.

What is claimed is:

1. A method of determining if unstable asphaltenes are present within a crude oil sample, the method comprising:
    obtaining a crude oil sample from a well;
    introducing the crude oil sample to an annulus formed in a cylindrical capacitor;
    applying, via a measuring device, an electrical voltage across the annulus and through the crude oil sample;
    measuring, via the measuring device, a dielectric constant of asphaltenes and desasphalted oil fractions of the crude oil sample;
    responsive to the measured dielectric constant, determining if unstable asphaltenes are present within the crude oil sample; and
    responsive to a determination that unstable asphaltenes are present in the crude oil sample in an amount above a predetermined value, mitigating asphaltene precipitation via addition of a chemical additive to the well.

2. The method of claim 1, further comprising providing a signal responsive to the determination that unstable asphaltenes are present in the crude oil sample in the amount above the predetermined value.

3. The method of claim 1, wherein the method is performed on a periodic time interval.

4. The method of claim 1, wherein the determining if unstable asphaltenes are present within the crude oil sample comprises calculating a modified Lowry parameter.

5. The method of claim 1, wherein the determining if unstable asphaltenes are present within the crude oil sample comprises calculating a modified Wu parameter.

6. The method of claim 1, further comprising performing a fractional analysis of the crude oil sample in order to obtain a volume fraction of asphaltenes and deasphalted oil present in the crude oil sample.

7. The method of claim 6, wherein the determining if unstable asphaltenes are present within the crude oil sample comprises calculating a colloidal stability index.

8. The method of claim 1, further comprising determining, based on the determination that unstable asphaltenes are present in the crude oil sample in the amount above the predetermined value, a probability of asphaltene precipitation.

9. The method of claim 1, wherein the chemical additive is introduced to a region of the well proximate a wellhead.

10. A method of determining if unstable asphaltenes are present in a crude oil flow, the method comprising:
    placing a crude oil sample in an annulus formed in a cylindrical capacitor;
    performing a fractional analysis of the crude oil sample in order to obtain a volume fraction of asphaltenes and deasphalted oil present in the crude oil sample;
    determining a colloidal instability index of the crude oil sample;
    applying, via a measuring device, an electrical voltage across the annulus and through the crude oil sample;
    measuring, via the measuring device, a dielectric constant of the asphaltenes and the desasphalted oil fractions of the crude oil sample;
    responsive to the measured dielectric constant, determining if unstable asphaltenes are present within the crude oil sample; and
    responsive to a determination that unstable asphaltenes are present in the crude oil sample in an amount above a predetermined value, introducing a chemical additive to the crude oil flow to mitigate asphaltene instability in the crude oil flow.

11. The method of claim 10, wherein the chemical additive comprises aromatic hydrocarbons.

12. The method of claim 10, further comprising evaluating an efficacy of the chemical additive at mitigating asphaltene precipitation.

13. The method of claim 10, further comprising providing a signal responsive to the determination that unstable asphaltenes are present in the crude oil sample in the amount above the predetermined value.

14. The method of claim 10, wherein the determining if unstable asphaltenes are present within the crude oil sample comprises calculating a modified Lowry parameter.

15. The method of claim 10, wherein the determining if unstable asphaltenes are present within the crude oil sample comprises calculating a modified Wu parameter.

16. The method of claim 10, further comprising determining, based on the determination that unstable asphaltenes are present in the crude oil sample in the amount above the predetermined value, a probability of asphaltene precipitation.

17. A method of determining if unstable asphaltenes are present within a crude oil sample, the method comprising:
    obtaining a crude oil sample from a well;
    introducing the crude oil sample to an annulus formed in a cylindrical capacitor;
    applying, via a measuring device, an electrical voltage across the annulus and through the crude oil sample;
    measuring, via the measuring device, a dielectric constant of asphaltenes and desasphalted oil fractions of the crude oil sample;
    responsive to the measured dielectric constant, determining if unstable asphaltenes are present within the crude oil sample; and
    responsive to a determination that unstable asphaltenes are present in the crude oil sample in an amount above a predetermined value, mitigating asphaltene precipitation.

18. The method of claim 17, wherein the mitigating comprises modulating a pressure of the well in a region of the well proximate a wellhead.

19. The method of claim 17, wherein the mitigating comprises:
    modulating a pressure of the well in a region of the well proximate a wellhead; and
    injecting a chemical additive into the well in the region of the well proximate the wellhead.

20. The method of claim 17, wherein the mitigating comprises injecting a chemical additive into the well at a region of the well that is proximate a temperature change.

* * * * *